United States Patent
North et al.

(10) Patent No.: US 12,194,130 B2
(45) Date of Patent: Jan. 14, 2025

(54) ORAL CARE COMPOSITIONS AND METHODS FOR THE SAME

(71) Applicant: Colgate-Palmolive Company, New York, NY (US)

(72) Inventors: Michael North, Middlesex, NJ (US); Rong Dong, Highland Park, NJ (US); Paloma Pimenta, Staten Island, NY (US); Shira Pilch, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 125 days.

(21) Appl. No.: 17/682,840

(22) Filed: Feb. 28, 2022

(65) Prior Publication Data

US 2022/0175650 A1    Jun. 9, 2022

Related U.S. Application Data

(63) Continuation of application No. 16/161,143, filed on Oct. 16, 2018, now Pat. No. 11,260,016.

(51) Int. Cl.
| | |
|---|---|
| *A61K 8/81* | (2006.01) |
| *A61K 8/02* | (2006.01) |
| *A61K 8/73* | (2006.01) |
| *A61Q 11/00* | (2006.01) |

(52) U.S. Cl.
CPC .......... *A61K 8/8158* (2013.01); *A61K 8/0204* (2013.01); *A61K 8/731* (2013.01); *A61K 8/8152* (2013.01); *A61Q 11/00* (2013.01)

(58) Field of Classification Search
None
See application file for complete search history.

(56) References Cited

U.S. PATENT DOCUMENTS

| | | |
|---|---|---|
| 7,252,836 B2 | 8/2007 | Brown et al. |
| 7,862,802 B2 | 1/2011 | Kim et al. |
| 8,883,212 B2 | 11/2014 | Pillai et al. |
| 9,808,416 B2 | 11/2017 | Georges et al. |
| 10,123,953 B2 | 11/2018 | Ramji et al. |
| 2005/0281757 A1 | 12/2005 | Ibrahim et al. |
| 2006/0045854 A1* | 3/2006 | Zaidel .................. A61K 8/8176 424/53 |
| 2007/0196323 A1 | 8/2007 | Zhang et al. |
| 2008/0292669 A1 | 11/2008 | Deng et al. |
| 2014/0242001 A1* | 8/2014 | Pillai ....................... A61K 8/29 424/49 |
| 2016/0074290 A1 | 3/2016 | Sagel et al. |
| 2016/0220472 A1 | 8/2016 | Wang et al. |
| 2017/0049671 A1 | 2/2017 | Prencipe et al. |
| 2017/0128346 A1 | 5/2017 | Dong et al. |
| 2018/0193247 A1* | 7/2018 | Dong .................. A61K 8/0216 |
| 2018/0250205 A1 | 9/2018 | Pillai et al. |

FOREIGN PATENT DOCUMENTS

| | | |
|---|---|---|
| CN | 1418085 | 5/2003 |
| CN | 108348444 | 7/2018 |
| WO | 0168045 | 9/2001 |
| WO | 2017/030583 | 2/2017 |
| WO | 2018/060209 | 4/2018 |

OTHER PUBLICATIONS

International Search Report and the Written Opinion of the International Searching Authority issued in international application PCT/US2018/055971 mailed Feb. 27, 2019.

\* cited by examiner

*Primary Examiner* — Brian Gulledge

(57) ABSTRACT

Film forming compositions and methods for preventing stains and increasing shine and gloss of teeth. The film forming compositions may include a polymer, such as a hydrophobic polymer, and an orally acceptable solvent. The hydrophobic polymer may include an acrylate component and a hydrophobic group coupled with one another. The hydrophobic group may include an alkyl chain, a polyethylene glycol, a polypropylene, a polyester, a polyorthoester, a phospholipid, a long chain fatty acid, a vinyl chloride, fluorethylene, a siloxane, a urethane, an octylacrylamide, a butylaminoethyl, a styrene, and combinations thereof.

6 Claims, No Drawings

ORAL CARE COMPOSITIONS AND METHODS FOR THE SAME

CROSS REFERENCE TO RELATED APPLICATIONS

This application is a continuation of U.S. application Ser. No. 16/161,143, filed Oct. 16, 2018, the content which is incorporated herein by reference in its entirety.

BACKGROUND

Conventional oral care products, such as dentifrices, may often incorporate abrasives to clean plaque and stains from surfaces of teeth. In addition to removing plaque and stains, the abrasives may also be capable of polishing the teeth to thereby increase the gloss and shine thereof. While conventional oral care products incorporating abrasives have proven to be effective for removing plaque and stains and for increasing gloss and shine, the sustained use of these oral care products may often result in excessive abrading of enamel on the surfaces of the teeth.

What is needed, then, are improved oral care products and film forming compositions, and methods for protecting teeth from stains and/or improving gloss and shine of the teeth without abrasives.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a film forming composition for preventing stains or increasing shine and gloss of teeth. The film forming composition may include a polymer, such as a hydrophobic polymer, and an orally acceptable solvent.

In at least one implementation, the hydrophobic polymer may include an acrylate component and a hydrophobic group coupled with one another. The hydrophobic group may include one or more of an alkyl chain, a polyethylene glycol, a polypropylene, a polyester, a polyorthoester, a phospholipid, a long chain fatty acid, a vinyl chloride, fluorethylene, a siloxane, a urethane, an octylacrylamide, a butylaminoethyl, and a styrene.

In at least one implementation, the acrylate component may be provided by an acrylate monomer. The acrylate monomer may include one or more of methyl acrylate, ethyl acrylate, 2-chloroethyl vinyl ether, 2-ethylhexyl acrylate, hydroxyethyl methacrylate, butyl acrylate, butyl methacrylate, and trimethylolpropane triacrylate. The acrylate component may be configured to facilitate, maintain, or increase adhesion of a film formed from the film forming composition to surfaces of the teeth.

In at least one implementation, the polymer may be a carboxylated acrylic copolymer.

In at least one implementation, the polymer may be a copolymer of octylacrylamide and one or more monomers. The one or more monomers may include one or more of acrylic acid, methacrylic acid, and any simple ester thereof. In at least one implementation, the polymer may be DERMACRYL®.

The foregoing and/or other aspects and utilities embodied in the present disclosure may be achieved by providing a film forming composition for increasing shine and gloss of teeth, the film forming composition may include a polycarboxylate polymer and an orally acceptable solvent. In at least one implementation, the polycarboxylate polymer may be a copolymer of methyl vinyl ether and maleic anhydride.

The foregoing and/or other aspects and utilities embodied in the present disclosure may be achieved by providing a film forming composition for increasing shine and gloss of teeth. The film forming composition may include an ethylcellulose having a degree of ethoxylation of about 45% to about 55% or about 48% to about 52%.

In at least one implementation, the film forming composition may further include a fluoride compound. The fluoride compound may be a soluble salt of a fluoride ion. In at least one implementation, the fluoride compound may include one or more of sodium fluoride, potassium fluoride, calcium fluoride, zinc fluoride, zinc ammonium fluoride, lithium fluoride, ammonium fluoride, stannous fluoride, and stannous fluorozirconate. In a preferred implementation, the fluoride compound includes sodium fluoride.

In at least one implementation, the orally acceptable solvent may include one or more of ethanol, methanol, isopropanol, butanol, water, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, and benzyl alcohol. In a preferred implementation, the orally acceptable solvent includes ethanol.

In at least one implementation, the film forming composition may further include an adhesive. The adhesive may include one or more of a polyvinyl acetaldehyde, a polyvinyl alcohol, a polyvinyl acetate, a poly(ethylene oxide), a polyacrylate, a polyvinylpyrolidone, a polyvinylpyrolidone/vinyl acetate copolymer, a polyoxyethylene/polyoxopropylene block copolymer, and a silicone resin.

In at least one implementation, the film forming composition may further include one or more of a therapeutic agent, an antimicrobial agent, a desensitizing agent, a sweetener, and a whitening agent.

In at least one implementation, the whitening agent includes an oxidizing agent, optionally, the oxidizing agent includes one or more of peroxides, chlorites, and hypochlorites. In at least one implementation, the whitening agent includes a peroxide compound.

The foregoing and/or other aspects and utilities embodied in the present disclosure may be achieved by providing a method for preventing stains on teeth. The method may include applying any one of the film forming composition disclosed herein on or to surfaces of the teeth. The method may also include evaporating at least a portion of the orally acceptable solvent to form a film on the surfaces of the teeth.

The foregoing and/or other aspects and utilities embodied in the present disclosure may be achieved by providing a method for increasing shine and gloss of teeth. The method may include applying any one of the film forming composition disclosed herein on or to surfaces of the teeth. The method may also include evaporating at least a portion of the orally acceptable solvent to form a film on the surfaces of the teeth.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range All references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that films formed from polymers including an acrylate component and a bulky hydrophobic group exhibit relatively greater efficacy for both stain prevention and as a stain barrier as compared to polymers without these characteristics or properties. In some examples, the relatively bulky hydrophobic group may be coupled with the acrylate. For example, films formed from a copolymer of an acrylate monomer and a monomer having a relatively bulky hydrophobic functional group, such as an octylacrylamide, a butylaminoethyl, and/or a styrene exhibit relatively greater efficacy for both stain prevention and as a stain barrier as compared to films formed from a polymer without these properties. It was also surprisingly and unexpectedly discovered that films formed from polymers incorporating or including acrylic acid or acrylate groups exhibit relatively greater binding to surfaces of the teeth as compared to films formed from polymers without acrylic acid groups. It was further surprisingly and unexpectedly discovered that films formed from polymers incorporating or including acrylic acid groups exhibit relatively greater and more reproducible or consistent gloss and shine properties as compared to films formed from polymers without acrylic acid groups.

Compositions

Compositions disclosed herein may be or include an oral care product or a film forming composition thereof. For example, the compositions disclosed herein may be an oral care product including the film forming composition, or the film forming composition thereof. In at least one implementation, the film forming composition may include one or more polymers having a hydrophilic component or functional group and a hydrophobic component or functional group. For example, the film forming composition may include a polymer having an acrylate or acrylic acid component (i.e., hydrophilic component) and a bulky hydrophobic component, such as a tert-octylacrylamide, a butylaminoethyl methacrylate and/or a styrene. As further described herein, the film forming compositions disclosed herein or the films formed therefrom may be capable of or configured to provide stain barrier and stain prevention properties to surfaces of the oral cavity, such as surfaces of teeth. The film forming compositions disclosed herein or the films formed therefrom may also be capable of or configured to enhance, maintain, or otherwise provide gloss and shine to surfaces of the teeth.

Polymers

The one or more polymers of the film forming composition may be or include, but are not limited to, one or more film forming polymers. As used herein, the expression "film forming polymer" may refer to or encompass polymers, prepolymers, and/or monomers capable of or configured to forming, either alone or in the presence of at least one additional agent, a continuous film on a substrate, such as the surfaces of the oral cavity (e.g., surface of teeth).

The film forming polymer may include one or more hydrophilic components or functional groups and/or one or more hydrophobic components or functional groups. The hydrophilic components or functional groups may be capable of or configured to facilitate, maintain, or increase the adhesion of the film forming polymer to surfaces of the oral cavity. Illustrative hydrophilic components or functional groups may be or include, but are not limited to, acrylate or acrylic acid groups, carboxyl groups, carbonyl groups, sulfhydryl groups, phosphate groups, hydroxyl groups, amines, disulfides, nitro groups, or the like, and combinations thereof. The hydrophilic components may be provided by one or more acrylate monomers. Illustrative acrylate monomers may include, but are not limited to, methacrylates, methyl acrylate, ethyl acrylate, 2-chloroethyl vinyl ether, 2-ethylhexyl acrylate, hydroxyethyl methacrylate, butyl acrylate, butyl methacrylate, trimethylolpropane triacrylate, or the like, and mixtures or combinations thereof.

The hydrophobic components or functional groups may be capable of or configured to provide one or more benefits or properties to the film formed by the film forming polymer. For example, the hydrophobic components may be capable of or configured to provide, maintain, or increase the efficacy of the film for stain prevention. In another example, the hydrophobic component may be capable of or configured to provide, maintain, or increase the efficacy of the film as a stain barrier. Illustrative hydrophobic components or functional groups may be or include, but are not limited to, an alkyl chain, a polyethylene glycol, a polypropylene, a polyester, a polyorthoester, a phospholipid, a long chain fatty acid, a vinyl chloride, fluorethylene, a siloxane, a urethane, an octylacrylamide, a butylaminoethyl, a styrene, or the like, and mixtures or combinations thereof.

In at least one implementation, the film forming polymer may be or include a homopolymer. In another implementation, the film forming polymer may be or include a copolymer composed of or produced by two or more dissimilar monomers. For example, the film forming polymer may be or include a copolymer composed of a first monomer capable of or configured to provide the hydrophilic component or functional group and a second monomer capable of or configured to provide the hydrophobic component or functional group.

In at least one implementation, the film forming polymer may be or include a carboxylated acrylic copolymer. For example, the film forming polymer may be a copolymer of octylacrylamide and one or more monomers, where the one or more monomers may include one or more of acrylic acid, methacrylic acid, and any one or more simple esters thereof. In another example, the film forming polymer may be a polymer formed from octylacrylamide, t-butylaminoethyl methacrylate, and one or more monomers of acrylic acid, methacrylic acid, or any one or more simple esters thereof.

Illustrative film forming polymer may be or include, but are not limited to, those sold under the trade names DERMACRYL®, AMPHOMER®, BALANCE®, and VERSACRYL®, which are commercially available from AkzoNobel Company, Surface Chemistry of Amsterdam, Netherlands. For example, the film forming polymer may be or include, but are not limited to, AMPHOMER® 4961, AMPHOMER® HC, DERMACRYL® 2.0, RESYN™ XP, a film forming polymer selected from octylacrylamide/acrylates/butylaminoethyl methacrylate copolymer, such as AMPHOMER® LV-71, AMPHOMER®, AMPHOMER® EDGE™, BALANCE® 47, or the like, and combinations thereof, all of which are commercially available from AkzoNobel Company, Surface Chemistry of Amsterdam, Netherlands. The film forming polymer may be selected from vinyl acetate/butyl maleate/isobornyl acrylate copolymers, such as ADVANTAGE™ PLUS from Ashland Global Specialty Chemicals Inc. of Covington, KY The film forming polymer may also be selected from acrylates/t-butylacrylamide copolymers, such as ULTRAHOLD® STRONG and ULTRAHOLD®8 from BASF SE of Ludwigshafen, Germany. The film forming polymer may also be selected from acrylates/dimethylaminoethyl methacrylate copolymers, such as the EUDRAGIT® range of polymers from Evonik Industries of Essen, Germany, such as EUDRAGIT®E100, EUDRAGIT® E PO (CAS: 24938-16-7), EUDRAGIT® RS 100, EUDRAGIT® RS PO, EUDRAGIT® RL PO, EUDRAGIT® RL 100, or the like, and combinations thereof. For example, the film forming polymer may be poly(butyl methacrylate-co-(2-dimethylaminoethyl) methacrylate-co-methyl methacrylate) 1:2:1. The film forming polymer may be selected from polyvinylpyrrolidone/vinyl acetate, such as the PVPNA series of polymers, and triacontanyl PVP, such as GANEX™ WP-660, both of which are commercially available from Ashland Global Specialty Chemicals Inc. of Covington, KY The film forming polymer may be selected from at least one of octylacrylamide/acrylates/butylaminoethyl methacrylate copolymer, vinyl acetate (VA)/butyl maleate/isobornyl acrylate copolymer, acrylates/t-butylacrylamide copolymer, polyvinylpyrrolidone/vinyl acetate copolymer, triacontanyl PVP copolymer, acrylates/dimethylaminoethyl methacrylate copolymer, and the like, and mixtures or combinations thereof. In an preferred implementation, the film forming polymer may be a copolymer of acrylates and octylacrylamide. For example, the film forming polymer may be or include copolymer 2-propenoic acid, 2-methyl-, 2-methylpropylester, polymer with 2-propenoic acid and N-(1,1,3,3-tetramethylbutyl)-2-propenamide or 2-propenoic acid, 2-methyl-, 2-methylpropyl ester, 2-propenoic acid, N-(1,1,3,3-tetramethylbutyl)-2-propenamide (CAS 129702-02-9). For example, the film forming polymer may be or include, but is not limited to, DERMACRYL® 79, which is commercially available from AkzoNobel Company, Surface Chemistry of Amsterdam, Netherlands. In another preferred implementation, the film forming polymer may be an oxtylacrylamide/acrylates/butylaminoethyl methacrylate copolymer. For example, the film forming polymer may be or include copolymer 2-Propenoic acid, 2-methyl-, 2-(1,1-dimethylethyl)aminoethyl ester, polymer with methyl 2-methyl-2-propenoate, 1,2-propanediol mono(2-methyl-2-propenoate), 2-propenoic acid and N-(1,1,3,3-tetramethylbutyl)-2-propenamide (CAS 70801-07-09). For example, the film forming polymer may be or include, but is not limited to AMPHOMER® LV-71, commercially available from AkzoNobel Company, Surface Chemistry. In yet another preferred implementation, the film forming polymer may be EUDRAGIT® E PO (CAS: 24938-16-7).

In at least one implementation, the film forming polymer may be or include, but is not limited to a polycarboxylate, such as a copolymer of methyl vinyl ether and maleic anhydride. For example, the film forming polymer may be or include an anionic polycarboxylate polymer, such as GANTREZ® S-97, commercially available from Ashland Specialty Chemicals of Bound Brook. N.J.

In another implementation, the film forming polymer may be or include, but is not limited to, a styrene copolymer, such as poly(styrene-co-maleic acid) partial isobutyl ester copolymer (CAS 28571-95-1).

In at least one implementation, the film forming polymer may be or include, but is not limited to, a derivative of cellulose or cellulose derivative, such as an alkyl cellulose ether. As used herein, the expression "alkyl cellulose ether" may refer to a lower alkyl ether of cellulose, such as an ethyl cellulose. In a preferred implementation, the cellulose derivative is ethyl cellulose. The degree of ethoxylation and/or the viscosity of the ethyl cellulose may vary. For example, the ethyl cellulose may have a degree of ethoxylation of about 45% to about 55%, or about 48% to about 52%. In another example, the ethyl cellulose may have a viscosity of about 3 cP to about 70 cP or about 80 cP to about 105 cP (5% 80:20 toluene:ethanol solution measured at 25° C.). In another example, the ethyl cellulose may have an average substitution value of about 2.3 to about 2.60 ethoxyl groups per anhydroglucose unit. In yet another example, the ethyl cellulose may have an average substitution value of about 2.46 to about 2.58 ethoxyl groups per anhydroglucose unit, corresponding to an ethoxyl content of about 48% to about 49.5%. Illustrative ethyl celluloses may be or include, but are not limited to, AQUALON® EC N100 ethyl cellulose, commercially available from Hercules Inc. of Wilmington, DE, ETHOCEL® Standard 100, ETHOCEL™ E7, ETHOCEL™ E22, ETHOCEL™ E50, or the like, and mixtures thereof, all of which are commercially available from the Dow Corning Company.

The amount or concentration of any one or more of the film forming polymers present in the oral care product or the film forming composition thereof may vary widely. In at least one implementation, the amount of any one or more of the film forming polymers present may be an amount effective to form a film capable of or configured to prevent the penetration of stains therethrough and/or an amount effect to form a film capable of or configured to provide a stain barrier. In another implementation, the amount of the any one or more of the film forming polymers present may be an amount effective to form a film capable of or configured to provide relatively greater gloss and shine to a substrate (e.g., surfaces of teeth) as compared to the substrate alone. In at least one implementation, the amount of any one or more of the film forming polymers present may be from about 1 weight % to about 50 weight %, based on a total weight of the oral care product or the film forming composition thereof. For example, the amount of any one or more of the film forming polymers present may be from about 1 weight %, about 2 weight %, about 4 weight %, about 6 weight %, about 8 weight %, about 10 weight %, about 12 weight %, about 14 weight %, about 16 weight %, about 18 weight %, about 20 weight %, about 22 weight %, or about 24 weight % to about 26 weight %, about 28 weight %, about 30 weight %, about 32 weight %, about 34 weight %, about 36 weight %, about 38 weight %, about 40 weight %, about 42 weight %, about 44 weight %, about 46 weight %, about 48 weight %, or about 50 weight %, based on a total weight of the oral care product or the film forming composition thereof. In another example, the amount of any one or more of the film forming polymers present may be from about 1 weight % to about 50 weight %, about 5 weight % to about 45 weight %, about 10 weight % to about 40 weight %, about 15 weight % to about 35 weight %, about 20 weight % to about 30 weight %, or about 22.5 to about 28.5, or about 25 weight %. In another implementation, the amount of any one or more of the film forming polymers present may be from about 1 weight % to about 30 weight %, based on a total weight of the oral care product or the film forming composition thereof. For example, the amount of any one or more of the film forming polymers present may be from about 1 weight %, about 2 weight %, about 4 weight %, about 6 weight %, about 8 weight %, about 10 weight %, about 12 weight %, or about 14 weight % to about 16 weight %, about 18 weight %, about 20 weight %, about 22 weight %, about 24 weight %, about 26 weight %, about 28 weight %, or about 30 weight %, based on a total weight of the oral care product or the film forming composition thereof. In another example, the amount of any one or more of the film forming polymers present may be from about 1 weight % to about 30 weight %, about 2 weight % to about 28 weight %, about 4 weight % to about 26 weight %, about 6 weight % to about 24 weight %, about 8 weight % to about 22 weight %, about 10 weight % to about 20 weight %, about 12 weight % to about 18 weight %, or about 14 weight % to about 16 weight %.

Fluoride or Fluoride Compounds

The oral care product or the film forming composition thereof may include one or more fluorides or fluoride compounds. As used herein, the expression "fluoride" or "fluoride compound" may refer to a source of fluoride and/or compounds capable of or configured to provide fluoride ions. Illustrated fluorides may be or include, but are not limited to, soluble salts of the fluoride ion, such as sodium fluoride, potassium fluoride, calcium fluoride, zinc fluoride, zinc ammonium fluoride, lithium fluoride, ammonium fluoride, stannous fluoride, stannous fluorozirconate, complex fluorides, monofluorophosphates and salts thereof (e.g., sodium monofluorophosphate or potassium monofluorophosphate), laurylamine hydrofluoride, diethylaminoethyl-octoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, amine fluorides, or the like, and mixtures or combinations thereof. In a preferred implementation, the fluoride is sodium fluoride.

The amount or concentration of the one or more fluoride compounds present in the oral care product or the film forming composition thereof may vary widely. In at least one implementation, the fluoride compounds may be presented in an amount capable of or configured to provide fluoride ions in an amount of from about 100 ppm to about 50,000 ppm. For example, the fluoride compounds may be presented in an amount capable of or configured to provide fluoride ions in an amount of from about 100 ppm, about 500 ppm, about 1,000 ppm, about 5,000 ppm, or about 10,000 ppm to about 15,000 ppm, about 20,000 ppm, about 25,000 ppm, about 30,000 ppm, about 35,000 ppm, about 40,000 ppm, about 45,000 ppm, or about 50,000 ppm. In another example, the fluoride compounds may be presented in an amount capable of or configured to provide fluoride ions in an amount of at least 100 ppm, at least 500 ppm, at least 1,000 ppm, at least 5,000 ppm, at least 10,000 ppm, at least 15,000 ppm, at least 20,000 ppm, at least 25,000 ppm, or at least 30,000 ppm. In a preferred implementation, the fluoride compounds are present in an amount sufficient to provide from about 500 ppm to about 30,000 ppm, more preferably about 1,000 ppm to about 23,000 ppm, or about 1,100 ppm to about 22,600 ppm. It should be appreciated that the exact weight percentage of the fluoride compound in the film forming composition may be at least partially determined by the stoichiometric properties of the varying fluoride compounds. In an exemplary implementation, the fluoride compound is sodium fluoride and is present in an amount of from about 0.5 weight %, about 1 weight %, about 1.5 weight %, about 2 weight %, about 2.5 weight %, about 3 weight %, about 3.5 weight %, about 4 weight %, or about 4.5 weight % to about 5 weight %, about 6.5 weight %, about 7 weight %, about 7.5 weight %, about 8 weight %, or about 8.5 weight %. In a preferred implementation, the sodium fluoride is present in an amount of from about 4 weight % to about 6 weight %, or about 5 weight %. In another preferred implementation, the sodium fluoride is present in an amount of from about 0.5 weight % to about 1.5 weight %, about 1 weight %, or about 1.11 weight %.

Adhesive or Adhesion Enhancing Agent

In at least one implementation, the oral care product or the film forming composition thereof may optionally include one or more adhesives configured to improve, maintain, and/or facilitate the adhesion of the film formed from the film forming composition to surfaces of the oral cavity. The one or more adhesives may also be configured to increase the hydrophobicity of the film formed from the film forming composition, thereby allowing the film to withstand external challenges, such as abrading, rubbing, or brushing.

Illustrative adhesives may be or include, but are not limited to, alkyd resins, polyvinyl acetaldehydes, polyvinyl alcohols, polyvinyl acetates, poly(ethylene oxide), polyacrylates, ketone resins, polyvinylpyrolidone, polyvinylpyrolidone/vinyl acetate copolymer, polyethylene glycols of 200 to 1000 molecular weight, polyoxyethylene/polyoxopropylene block copolymers (Polyox), silicon resins, or the like, and mixtures or combinations thereof. In at least one implementation, the one or more adhesives may include siloxane polymers, which are also generally known in the art as "silicone" polymers. Illustrative silicone-based hydrophobic polymers may be or include, but are not limited to, polyorganosiloxane, polydiorganosiloxane, and the like, and combinations thereof. In at least one implementation, the adhesion enhancing agent includes at least one silicon pressure sensitive adhesive (PSA). Such PSAs may be pressure sensitive hydrophobic polymers specifically designed for pharmaceutical use and are permeable to many drug compounds and find application for the transdermal application of various compounds. In some implementations, the silicone polymers are the copolymer product of mixing a silanol terminated polydiorganosiloxane, such as polydimethyl siloxane, with a silanol-containing silicone resin, whereby the silanol groups of the polydiorganosiloxane undergo a condensation reaction with the silanol groups of the silicone resin such that the polydiorganosiloxane is lightly cross-linked by the silicone resin (that is, the polydiorganosiloxane chains are bonded together through the resin molecules to give chain branching and entanglement and/or a small amount of network character) to form the silicone hydrophobic polymers. In at least one implementation, the adhesion enhancing agents are available under the trade name BIO-PSA from the Dow Corning Company of Midland, MI The modification of a ratio of silicone resin to polydiorganosiloxane modifies the tackiness of the polymer. This ratio may be in the range of about 70:30 to about 50:50. For example, the BIO-PSA silicone commercially available from Dow-Corning is available in varying silicone resin to silicone polymer ratios, namely, 65/35 (low tack), 60/40 (medium tack), and 55/45 (high tack). Such a polyorganosiloxane PSA is available dissolved in either ethyl acetate solvent or dimethicone. In at least one implementation, the adhesion enhancing agent may include Silicone Adhesive 8-7016, commercially available from Dow Corning Corporation of Midland, MI.

In some implementations, the adhesive is a natural resin. Illustrative natural resins may be or include, but are not limited to, shellac, rosins, or the like, and mixtures or combinations thereof. Shellac is commercially available and may be provided with a solvent (e.g. ethanol). One such commercially available shellac, known as Refined Pharmaceutical Glaze, is available from Mantrose-Hacuser Co., Inc. of Westport, CT.

The amount or concentration of the adhesion enhancing agents present in the oral care product or the film forming composition thereof may vary widely. The amount of the adhesion enhancing agents present in the film forming composition may be from about 1 weight % to about 5 weight %. For example, the amount of the adhesion enhancing agents present in the film forming composition may be from about 1.0 weight %, about 1.5 weight %, about 2.0 weight %, about 2.5 weight %, or about 3.0 weight % to about 3.5 weight %, about 4.0 weight %, about 4.5 weight %, or about 5.0 weight %. In another example, the amount of the adhesion enhancing agents present in the film forming composition may be from about 1.0 weight % to about 5.0 weight %, about 1.5 weight % to about 4.5 weight %, about 2.0 weight % to about 4.0 weight %, or about 2.5 weight % to about 3.5 weight %. In yet another example, the amount of the adhesion enhancing agents present in the film forming composition may be greater than or equal to greater than or equal to 1.0 weight %, greater than or equal to 1.5 weight %, greater than or equal to 2.0 weight %, greater than or equal to 2.5 weight %, greater than or equal to 3.0 weight %, greater than or equal to 3.5 weight %, greater than or equal to 4.0 weight %, or greater than or equal to 4.5 weight %. In another example, the amount of the adhesion enhancing agents present in the film forming composition may be less than or equal to 1.0 weight %, less than or equal to 1.5 weight %, less than or equal to 2.0 weight %, less than or equal to 2.5 weight %, less than or equal to 3.0 weight %, less than or equal to 3.5 weight %, less than or equal to 4.0 weight %, less than or equal to 4.5 weight %, or less than or equal to 5.0 weight %. In a typical implementation, the amount of the adhesion enhancing agents present in the film forming composition is about 3.0 weight %.

Thickening System

In at least one implementation, the oral care product or the film forming composition thereof may optionally include a thickening system having one or more thickeners. The one or more thickeners may be any orally acceptable thickener or thickening agent. Illustrative thickeners may be or include, but are not limited to, colloidal silica, fumed silica, a cross-linked polyvinylpyrrolidone (PVP) polymer, cross-linked polyvinylpyrrolidone (PVP), and the like, and mixtures or combinations thereof. The thickening system may include a cross-linked polyvinylpyrrolidone (PVP) polymer. The thickening system may also include POLYPLASDONE® XL 10F, which is commercially available from Ashland Inc. of Covington, KY Additional illustrative thickeners may include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, MI), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, hydrophilic polymers, such as carbomers, such as carboxymethylene polymers, such as acrylic acid polymers, and acrylic acid copolymers, and the like, and mixtures or combinations thereof. Carboxypolymethylene is a slightly acidic vinyl polymer with active carboxyl groups. One such carboxypolymethylene is CARBOPOL® 974 and/or 980, commercially available from Noveon, Inc. of Cleveland, OH. In at least one implementation, the one or more thickeners may be or include a cellulose ether, selected from one or more of hydroxyalkyl cellulose polymers, such as hydroxypropyl methyl cellulose (HPMC), hydroxypropyl cellulose, hyrdoxyethyl cellulose, methyl cellulose, ethylcellulose, carboxymethyl cellulose, and mixtures or combinations thereof.

In at least one implementation, the thickening system may include a single thickener. For example, the thickening system may include the cross-linked polyvinylpyrrolidone (PVP) polymer. In another implementation, the thickening system may include a plurality of thickeners. For example, the thickening system may include the cross-linked PVP polymer and a silica thickener. In another example, the thickening system may include a plurality of silica thickeners.

The amount or concentration of the thickening system and/or the thickeners thereof present in the oral care product or the film forming composition thereof may vary widely. The amount of the thickening system and/or the thickeners thereof present in the oral care product or the film forming composition thereof may be from about 10 wt % to about 30 wt % based on the total weight of the oral care product or the film forming composition thereof. For example, the amount of the thickening system and/or the thickeners thereof present in the oral care product or the film forming composition thereof may be from about 10 wt %, about 11 wt %, about 12 wt %, about 13 wt %, about 14 wt %, about 15 wt %, about 16 wt %, about 17 wt %, about 18 wt %, about 19 wt %, about 20 wt %, or about 21 wt % to about 22 wt %, about 23 wt %, about 24 wt %, about 25 wt %, about 26 wt %, about 27 wt %, about 28 wt %, about 29 wt %, or about 30 wt %. In another example, the amount of the thickening system and/or the thickeners thereof present in the oral care product or the film forming composition thereof may be from about 12 wt % to about 30 wt %, about 13 wt % to about 29 wt %, about 14 wt % to about 28 wt %, about 15 wt % to about 27 wt %, about 16 wt % to about 26 wt %, about 17 wt % to about 25 wt %, about 18 wt % to about 24 wt %, about 19 wt % to about 23 wt %, or about 20 wt % to about 22 wt %. In a typical implementation, the amount of the thickening system and/or the thickeners thereof present in the oral care product or the film forming composition thereof may be from about 20 wt % to about 22 wt %, more typically about 21 wt %.

Flavoring Agents

The film forming composition may also include one or more flavoring agents. Illustrative flavoring agents that may be utilized in the film forming composition may be or include, but are not limited to, essential oils and various flavoring aldehydes, esters, alcohols, and similar materials, as well as sweeteners such as sodium saccharin, and the like, and mixtures or combinations thereof. Illustrative essential oils may include, but are not limited to, oils of spearmint, peppermint, wintergreen, sassafras, clove, sage, eucalyptus, marjoram, cinnamon, lemon, lime, grapefruit, and orange. Also useful are chemicals such as menthol, carvone, anethole, and the like, and mixtures or combinations thereof. In a preferred implementation, the flavoring agents include oils of peppermint and spearmint.

The amount or concentration of the one or more flavoring agents present in the oral care product or the film forming composition thereof may vary widely. In at least one implementation, the amount of the one or more flavoring agents present may be from about 0.01 weight % to about 50 weight %, based on a total weight of the oral care product or the film forming composition thereof. For example, the amount of the one or more flavoring agents present may be from about 0.01 weight %, about 1 weight %, about 5 weight %, about 10 weight %, about 15 weight %, about 20 weight %, or about 25 weight % to about 30 weight %, about 35 weight %, about 40 weight %, about 45 weight %, or about 50 weight %.

Orally Acceptable Vehicle

In at least one implementation, the film forming composition may be dispersed or dissolved in an orally acceptable vehicle. As used herein, the expression "orally acceptable vehicle" may refer to a suitable vehicle, ingredient, or combination of ingredients, which can be used to form and/or apply the film forming composition or one or more components thereof to surfaces of the oral cavity in a safe and effective manner. For example, the orally acceptable vehicle may be a suitable solvent, and the film forming composition may be dispersed, dissolved, mixed, or otherwise contacted with the suitable solvent to prepare or form the oral care product. Illustrative solvents may be or include, but are not limited to, ethanol, methanol, isopropanol, butanol, water, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, benzyl alcohol, or the like, and mixtures or combinations thereof. In a preferred implementation, the orally acceptable vehicle is ethanol.

The orally acceptable vehicle may make up the balance of the oral care product. In at least one implementation, the orally acceptable vehicle (e.g., ethanol) may be present in an amount of at least 60 weight %, at least 62 weight %, at least 64 weight %, at least 66 weight %, at least 68 weight %, at least 70 weight %, at least 72 weight %, at least 74 weight %, at least 76 weight %, at least 78 weight %, at least 80 weight %, at least 82 weight %, at least 84 weight %, at least 86 weight %, at least 88 weight %, at least 90 weight %, at least 92 weight %, at least 94 weight %, at least 96 weight %, at least 98 weight %, or at least 99 weight %, based on a total weight of the oral care product.

Additional Ingredients

It should be appreciated by one having ordinary skill in the art, that the oral care products and/or the film forming compositions thereof may include other additional ingredients/components. For example, the oral care products and/or the film forming compositions thereof may include one or more anti-caries agents, desensitizing agents, viscosity modifiers, diluents, surface active agents (e.g., emulsifiers, foam modulators, etc.), pH modifying agents (e.g., acids and bases), therapeutic agents, humectants, mouth feel agents, sweetening agents, flavor agents, whitening agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials.

As discussed above, the film forming composition may include one or more therapeutic agents. Illustrative therapeutic agents may be or include, but are not limited to, a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

The therapeutic agent may also be or include, but are not limited to, an antimicrobial (e.g., antibacterial) agent, such as triclosan. An illustrative list of suitable antibacterial agents is provided in U.S. Pat. No. 5,776,435 to Gaffar et al., the contents of which are incorporated herein by reference. One or more antimicrobial agents may be present in an antimicrobial effective total amount of about 0.05% to about 10%, for example about 0.1% to about 3%.

Other therapeutic agents include without limitation calcium ion sources, e.g. calcium carbonate, a zinc ion source, e.g., zinc citrate, a potassium ion source, e.g., potassium chloride or combinations thereof. If present, the amount of ion source in the present composition ranges from about 0.1% to 5%, typically about 1% by weight. A basic amino acid, e.g., arginine in free or salt form, may also be used as a therapeutic agent.

As discussed above, the film forming composition may include one or more whitening agents. As used herein, the expression "whitening agent" may refer to a material that affects the whitening of a tooth surface to which it is applied. Any whitening agent known or developed in the art may be used in the present film forming composition.

For example, in some implementations, the film forming composition may include a whitening pigment. In some implementations, the whitening pigments include particles ranging in size from about 0.1 µm to about 10 µm with a refractive index greater than about 1.2. Suitable whitening agents include, without limitation, titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxylapatite particles, calcium carbonate particles, zinc phosphate particles, silicon dioxide particles, zirconium silicate particles and combinations thereof. The whitening pigment, such as titanium dioxide particles, may be in an amount that is sufficient to whiten the teeth.

In some implementations, the whitening agent may be an oxidizing agent, a reducing agent, or combinations thereof. As used herein, the expression "oxidizing agent" may refer to material and/or compounds that can accept an electron from another material and/or compound (e.g., molecule) in the environment of the oral cavity without having a deleterious or unacceptably harmful effect on the oral cavity in normal and accepted use. Illustrative oxidizing agents suitable for use with the film forming composition may include, but are not limited to, peroxides, chlorites and hypochlorites. Examples of suitable chlorites and hypochlorites include those having alkali or alkaline metal cations and include calcium chlorite, barium chlorite, magnesium chlorite, lithium chlorite, sodium chlorite, potassium chlorite, calcium hypochlorite, barium hypochlorite, magnesium hypochlorite, lithium hypochlorite, lithium hypochlorite, and sodium hypochlorite.

In at least one implementation, the whitening agent includes a peroxide compound. As used herein, the expression "peroxide compound" may refer to any compound including a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and mixtures thereof. Peroxy acids and their salts include organic peroxy acids, such as alkyl peroxy acids and monoperoxyphthalate and mixtures thereof, as well as inorganic peroxy acid salts, such as persulfate, dipersulfate, percarbonate, perphosphate, perborate and persilicate salts of alkali and alkaline earth metals such as lithium, potassium, sodium, magnesium, calcium and barium, and mixtures thereof. Typically, the peroxide compound comprises hydrogen peroxide, urea peroxide, sodium percarbonate or mixtures thereof.

In at least one implementation, the film forming compositions include a whitening complex. As used herein, the expression "whitening complex" may refer to a whitening agent as described herein complexed with a polymer or copolymer that is capable of or configured to release the whitening agent upon exposure to highly aqueous environments, such as in the oral cavity. As used herein, a "complex" is an entity formed by a loose association involving two or more molecular entities (ionic or uncharged), e.g., a whitening agent and a polymer.

All ingredients for use in the compositions described herein should be orally acceptable. As used herein, "orally acceptable" may refer to any ingredient that is present in a composition as described in an amount and form that does not render the composition unsafe for use in the oral cavity.

Methods

The present disclosure may provide methods for increasing shine and gloss, preventing stains, and/or providing a stain barrier on surfaces of an oral cavity in a human or animal subject. As used herein "animal subject" may include higher order non-human mammals such as canines, felines, and horses. The method may include contacting any one of the film forming compositions disclosed herein with surfaces of the oral cavity, such as surfaces of teeth. Contacting the surface of the teeth with the film forming composition may include applying the film forming composition directly to the teeth using a delivery device, such as a pen. (e.g., a COLGATE® whitening pen or a COLGATE® ACTIS™ whitening pen. Colgate-Palmolive Company. New York, NY), a liquid stick having an applicator, such as a felt tip, brush, spray, roller ball, or non-woven pad, or the like. Contacting the surface of the teeth with the film forming composition may also include disposing the film forming composition in a dental tray (e.g., reservoir of a dental tray) and disposing the dental tray about the teeth.

The method may also include evaporating a solvent or orally acceptable vehicle from the film forming composition to form a film on the surfaces of the teeth. The resulting film, formed in situ, may increase shine and gloss or perceived shine and gloss of the surfaces of the teeth, prevent stains on the surfaces of the teeth, and/or provide a stain barrier on surfaces of the teeth. The method may include include maintaining the film on the surfaces of the teeth for at least 12 hours, at least one day, at least two days, at least three days, at least four days, or more.

The method may include applying or contacting the oral care product and/or the film forming composition thereof with the surfaces of the teeth at predetermined intervals. For example, the method may include applying or contacting the oral care product and/or the film forming composition thereof with the surfaces of the teeth on a daily basis, every other day, once or twice a week, or once a month. In another example, the method may include applying or contacting the oral care product and/or the film forming composition thereof with the surfaces of the teeth at least once a day, at least once every two days, at least once every three days, at least once every five days, at least once a week, at least once every two weeks, or at least once a month. The oral care product and/or the film forming composition thereof may be utilized for up to 2 weeks, up to 3 weeks, up to 4 weeks, up to 6 weeks, up to 8 weeks, or greater.

All ingredients for use in the compositions described herein should be orally acceptable. As used herein, "orally acceptable" may refer any ingredient that is present in a composition as described in an amount and form which does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The ability or efficacy of films formed from varying test film forming compositions (1)-(9) was evaluated for stain prevention. The test film forming compositions (1)-(9) were prepared by combining about 80 weight % absolute ethanol (200 proof) with about 20 weight % of each of the following polymers: (1) Anionic Linear Polycarboxylate Polymer (GANTREZ®); (2) Poly(ethyl acrylate/acrylic acid) (P(EA/AA)); (3) Poly(styrene-co-maleic acid) partial isobutyl ester copolymer (Sty/Mal); (4) Acrylates/Octylacrylamide Copolymer (DERMACRYL® 79); (5) Octylacrylamide/Acrylates/Butylaminoethyl Methacrylate Copolymer (AMPHOMER®); (6) Acrylates/Dimethylaminoethyl Methacrylate Copolymer (EUDRAGIT® E PO) Copolymer; (7) Polyurethane-64 (BAYCUSAN® C 2000); (8) Poly methyl vinyl ether solution (PVME); and (9) Polydimethylsiloxane/Dimethicone (Dow Corning® Q7-9120 Silicone Fluid). Particularly, about 20 weight % of each of the polymers was combined with about 80 weight % of ethanol in a vial and vortexed or agitated for about 5 minutes to prepare respective solutions of each of the polymers. The solutions were then allowed to rest overnight and subsequently vortexed or agitated again for about 5 minutes.

To evaluate stain prevention, 36 artificially stained bovine incisors individually mounted to resin blocks and having L values between 64 and 74 were obtained from Therametric Technologies Inc. of Noblesville, IN Each of the artificially stained bovine incisors was cleaned and dried, and the baseline L*, a*, b* values of each of the 36 bovine incisors were recorded with a spectrophotometer (SPECTROSHADE Micro instrument manufactured by Medical High Technology of Verona, Italy). After measuring the L*, a*, b* values, each of the bovine incisors was incubated overnight in well plates containing simulated saliva at about 37° C. under stirring (about 100 rpm). After incubation, each of the bovine incisors was triple rinsed with deionized water and the L*, a*, b* values were measured with the spectrophotometer.

Each of the test film forming compositions (1)-(9) was applied to three separate bovine incisors to evaluate the stain prevention in triplicate, and the remaining nine bovine incisors were left uncoated to provide a negative control. To coat the bovine incisors, each of the test film forming compositions (1)-(9) was applied to a respective bovine incisor and allowed to air dry for about 2 minutes.

A staining broth was prepared by filtering wine through a fine mesh filter, steeping one LIPTON® black tea bag in 50 g of hot DI water for at least 15 minutes, and dissolving 1 g of instant coffee in 50 g of hot DI water for at least 15 minutes. The wine, tea, and coffee solutions were then combined with one another in equal parts by volume and stirred to prepare the staining broth. Each of the coated bovine incisors and the uncoated bovine incisors (Control) was then submerged in the staining broth and incubated at about 37° C. for about 24 hours under stirring (about 100 rpm).

Each of the bovine incisors was then removed from the staining broth and triple rinsed with DI water. It should be appreciated that rinsing the bovine incisors with the DI water allowed the respective film formed from each of the film forming compositions (1)-(9) to remain intact. The L*, a*, b* values of each of the bovine incisors after treatment were then measured. After measuring, each of the bovine incisors was then triple rinsed with ethanol to remove the respective films therefrom, and L*, a*, b* values were again measured after removal of the respective films.

The L*, a*, b* values after treatment were compared to the baseline values to calculate the change in the whiteness of each of the bovine incisors. It should be appreciated that the whiteness index (W*) is a measure of overall color change relative to pure white, and is given by formula (1), and the change in whiteness index (ΔW*) is measured by formula (2). It should further be appreciated that the lower the ΔW* the whiter the tooth.

The efficacy of each of the film forming compositions (1)-(9) and the control for stain prevention (ΔW*) and as a stain barrier (ΔW*) is summarized in Table 1. The stain barrier (ΔW*) values correspond to the L*, a*, b* values measured after rinsing with DI water (films still intact), and represent the efficacy of the films as a barrier to stains. It should be appreciated that stain barrier (ΔW*) values relatively lower than the control indicate the ability to partially or completely repel stains. The stain prevention (ΔW*) corresponds to the L*, a*, b* values measured after the film was removed with the ethanol rinse, and represents the efficacy of the films to capture or retain any stains that it was not able to repel.

$$W^* = ((L^*-100)^2 + (a^*)^2 + (b^*)^2)^{1/2} \quad (1)$$

$$\Delta W^* = W^*_{treated} - W^*_{baseline} \quad (2)$$

TABLE 1

Whitening Efficacy (ΔW*) for Stain Prevention and Stain Barrier for Film Forming Compositions (1)-(9)

| Sample | Stain Prevention (ΔW*) | Stain Barrier (ΔW*) |
|---|---|---|
| (C1) Control | 23.8 ± 6.8 | 23.8 ± 6.8 |
| (1) Anionic Linear Polycarboxylate Polymer (GANTREZ ®) | 3.6 ± 0.45 | 6.2 ± 1.3 |
| (2) Poly(ethyl acrylate/acrylic acid) (P(EA/AA)) | 7.3 ± 3.9 | 39.6 ± 1.7 |
| (3) Poly(styrene-co-maleic acid) partial isobutyl ester copolymer (Sty/Mal) | 1.9 ± 2.6 | 5.8 ± 1.6 |
| (4) Acrylates/Octylacrylamide Copolymer (DERMACRYL ® 79) | −0.12 ± 0.27 | −12.0 ± 7.3 |
| (5) Octylacrylamide/Acrylates/Butylaminoethyl Methacrylate Copolymer (AMPHOMER ®) | −1.8 ± 2.0 | −4.7 ± 1.1 |
| (6) Acrylates/Dimethylaminoethyl Methacrylate Copolymer (EUDRAGIT ® E PO) Copolymer | 6.1 ± 5.0 | 5.4 ± 3.4 |
| (7) Polyurethane-64 (BAYCUSAN ® C 2000) | 4.7 ± 2.9 | 24.3 ± 2.2 |
| (8) Poly(methyl vinyl ether) solution (PVME) | 8.8 ± 0.5 | 14.9 ± 1.8 |
| (9) Polydimethylsiloxane/Dimethicone (Dow Corning ® Q7-9120 Silicone Fluid) | 18.4 ± 1.7 | 20.5 ± 1.8 |

As illustrated in Table 1, test film forming compositions (4) and (5) provided a complete stain barrier, and test film forming compositions (1), (3), and (6) were able to repel a significant portion of the stain. It should be appreciated that each of the test film forming compositions (1) and (3)-(6) that exhibited relatively greater stain barrier properties has a combination of both hydrophilic and hydrophobic properties. It should be noted that poly(ethyl acrylate/acrylic acid) (P(EA/AA)) also exhibits both hydrophilic and hydrophobic properties, however, the film forming composition (2) exhibited relatively poor stain barrier properties. The discrepancy in the observed results of the film forming composition (2), however, was due to the fact that the dried film was colored and yielded false positives. As further illustrated in Table 1, the three remaining test film forming compositions. (7)-(9) are all hydrophobic polymers; and thus, exhibited relatively poor efficacy as a stain barrier. It should be noted that the film formed from polyurethane-64, similar to poly(ethyl acrylate/acrylic acid) (P(EA/AA)), exhibited a color that yielded a false positive.

To evaluate the efficacy of the films in trapping or retaining portions of the staining broth that the films failed to repel, the stain prevention values (ΔW*) were compared to the stain barrier values (ΔW*). Particularly, parity or substantially equal stain prevention and stain barrier values indicate relatively poor efficacy in trapping the stains that the films failed to repel. As illustrated in Table 1, the films formed from the film forming compositions (6) and (9) exhibited relatively poor efficacy in trapping the stains, indicating that these films allowed the stain to traverse directly to surfaces of the bovine incisors. The remaining films, however, exhibited relatively greater efficacy in preventing the stains from penetrating to surfaces of the bovine incisors.

Example 2

The efficacy of films formed from film forming compositions of Acrylates/Octylacrylamide Copolymer (DERMACRYL® 79) and Octylacrylamide/Acrylates/Butylaminoethyl Methacrylate Copolymer (AMPHOMER®) were evaluated for stain prevention at varying concentrations. Particularly, film forming compositions (10)-(14) including DERMACRYL® 79 and absolute ethanol as a solvent were prepared in the following concentrations: 1 weight %, 5 weight %, 10 weight %, 20 weight %, and 30 weight %. Film forming compositions (15)-(19) including AMPHOMER® in the same concentrations were similarly prepared.

To evaluate stain prevention, 33 artificially stained bovine incisors individually mounted to resin blocks and having L values between 66 and 78 were obtained from Therametric Technologies Inc. Each of the artificially stained bovine incisors was cleaned and dried, and the baseline L*, a*, b* values of each of the 33 bovine incisors were recorded with a spectrophotometer (SPECTROSHADE Micro instrument manufactured by Medical High Technology of Verona, Italy). After measuring the L*, a*, b* values, each of the bovine incisors was incubated overnight in well plates containing simulated saliva at about 37° C. under stirring (about 100 rpm). After incubation, each of the bovine incisors was triple rinsed with deionized water and the L*, a*, b* values were measured with the spectrophotometer.

Each of the test film forming compositions (10)-(14), having varying concentrations of DERMACRYL® 79, and the test film forming compositions (15)-(19), having varying concentrations of AMPHOMER®, was applied to three separate bovine incisors to evaluate the stain prevention in triplicate, and the remaining nine bovine incisors were left uncoated to provide a negative control. To coat the bovine incisors, each of the test film forming compositions (10)-(19) was applied to a respective bovine incisor and allowed to air dry for about 2 minutes.

The coated bovine incisors and the uncoated bovine incisors (Control) were then submerged in the staining broth of Example 1 and incubated at about 37° C. for about 24 hours under stirring (about 100 rpm). The bovine incisors were then removed from the staining broth and triple rinsed with DI water. As discussed above, rinsing the bovine incisors with the DI water allowed the respective film formed to remain intact. The L*, a*, b* values of the bovine incisors after treatment were then measured. After measuring, the bovine incisors were triple rinsed with ethanol to remove the respective films therefrom, and L*, a*, b* values were again measured after removal of the respective films. The efficacy of each of the film forming compositions (10)-(19) and the control for stain prevention (ΔW*) and as a stain barrier (ΔW*) is summarized in Table 2.

TABLE 2

Whitening Efficacy (ΔW*) for Stain Prevention for Film Forming Compositions (10)-(19)

| Sample | Stain Prevention (ΔW*) | Stain Barrier (ΔW*) |
|---|---|---|
| (C2) Control | 19.9 ± 3.7 | 20.7 ± 3.4 |
| (10) 1 weight % DERMACRYL ® 79 | 13.6 ± 11.5 | 14.6 ± 10.8 |
| (11) 5 weight % DERMACRYL ® 79 | 7.8 ± 7.8 | 8.5 ± 7.3 |
| (12) 10 weight % DERMACRYL ® 79 | 2.3 ± 2.5 | 2.1 ± 4.5 |
| (13) 20 weight % DERMACRYL ® 79 | −0.1 ± 0.7 | −4.4 ± 1.5 |
| (14) 30 weight % DERMACRYL ® 79 | −3.7 ± 2.7 | −5.6 ± 3.6 |
| (15) 1 weight % AMPHOMER ® | 16.0 ± 1.5 | 18.6 ± 1.9 |
| (16) 5 weight % AMPHOMER ® | 9.0 ± 7.8 | 12.6 ± 9.9 |
| (17) 10 weight % AMPHOMER ® | 0.5 ± 0.5 | 0.9 ± 2.4 |
| (18) 20 weight % AMPHOMER ® | −2.2 ± 4.0 | −5.1 ± 4.2 |
| (19) 30 weight % AMPHOMER ® | −3.4 ± 0.2 | −4.0 ± 3.5 |

As illustrated in Table 2, the film forming compositions including DEMACRYL®79 or AMPHOMER® at relatively low concentrations (about 1 weight % to about 5 weight %) exhibited lower efficacy for resisting staining as compared to the higher concentrations (about 10 weight % to about 30 weight %).

In view of the foregoing it was surprisingly and unexpectedly discovered that polymers including an acrylate component and a relatively bulky hydrophobic group coupled with the acrylate component exhibit relatively greater efficacy for both stain prevention and as a stain barrier as compared to polymers not having these properties. For example, the polymer may be a copolymer formed from an acrylate monomer and a monomer having a relatively bulky hydrophobic functional group, such as an octylacrylamide, a butylaminoethyl, and/or a styrene.

Example 3

The ability or efficacy of films formed from varying film forming compositions to provide gloss and/or shine on treated surfaces of teeth was evaluated. Particularly, film forming compositions including Acrylates/Octylacrylamide Copolymer (DERMACRYL® 79), Octylacrylamide/Acrylates/Butylaminoethyl Methacrylate Copolymer (AMPHOMER®), Poly(ethyl acrylate/acrylic acid) (P(EA/AA)), or ethylcellulose (AQUALON™ N100 Pharm) were evaluated for their ability to provide gloss and/or shine on surfaces of bleached bovine incisors obtained from Therametric Technologies, Inc. Film forming compositions (20)-(22) including DERMACRYL® 79 and absolute ethanol as a solvent were prepared in the following concentrations: 1 weight %, 10 weight %, and 20 weight %. Film forming compositions (23)-(25) including AMPHOMER®, film forming compositions (26)-(28) including P(EA/AA), and film forming compositions (29)-(31) including AQUALON™ N100 Pharm in the same concentrations (i.e., 1 weight %, 10 weight %, and 20 weight %) were similarly prepared.

Baseline gloss and shine measurements or Gloss Units (GU) were obtained on each of the bleached bovine incisors. To measure the baseline GU, each of the bovine incisors was placed facing downward toward the instrument (Novo-Curve Glossmeter manufactured by Rhopoint Instruments of East Sussex, UK) and covered to block ambient light. After an initial measurement of the GU, the bovine incisor was repositions, recovered, and measured again. This process was repeated for a total of three measurements, which were averaged to provide the baseline GU.

After the baseline GU of each of the bovine incisors was measured, each of the film forming compositions were applied to a respective bleached bovine incisor and dried for about 25 minutes. After application of the film forming composition, the GU was measured as discussed above. The change in GU or AGU is a measure of the change in Gloss Units (GU) and is calculated according to formula (3). It should be appreciated that a positive AGU indicates an increase in gloss and shine, and a decrease in AGU indicates a decrease in gloss and shine. Each sample was treated on six separate bovine incisors and averaged. The calculated AGU is summarized in Table 3.

$$\Delta GU = GU(\text{after application of film forming composition}) - GU(\text{baseline}) \quad (3)$$

TABLE 3

Gloss and Shine (ΔGU) for Film Forming Compositions (20)-(31)

| Sample | Gloss (ΔGU) |
|---|---|
| (20) 1 weight % DERMACRYL ® 79 | 6.4 ± 2.1 |
| (21) 10 weight % DERMACRYL ® 79 | 7.7 ± 9.4 |
| (22) 20 weight % DERMACRYL ® 79 | 4.9 ± 5.9 |
| (23) 1 weight % AMPHOMER ® | -3.6 ± 8.5 |
| (24) 10 weight % AMPHOMER ® | 11.0 ± 7.3 |
| (25) 20 weight % AMPHOMER ® | 14.4 ± 3.5 |
| (26) 1 weight % P(EA/AA) | 9.7 ± 16.3 |
| (27) 10 weight % P(EA/AA) | 8.7 ± 7.8 |
| (28) 20 weight % P(EA/AA) | 14.3 ± 10.4 |
| (29) 1 weight % AQUALON ™ EC N100 | 6.7 ± 13.3 |
| (30) 10 weight % AQUALON ™ EC N100 | 4.9 ± 2.7 |
| (31) 20 weight % AQUALON ™ EC N100 | -6.5 ± 8.9 |

As illustrated in Table 3, the films formed from the film forming compositions (23)-(25) including AMPHOMER® exhibited a significant increase in AGU as the concentration of the AMPHOMER® increased. As indicated, the film forming composition (23) including 1 weight % of AMPHOMER® exhibited little to no significant effect on gloss and shine; however, the films prepared from the 10 weight % and 20 weight % film forming compositions (24) and (25), respectively, exhibited a significant increase in AGU. It should be appreciated that the chemical structure of AMPHOMER® is ionic or has ionic charges provided by a carboxylate functional group of the acrylic acid or acrylate group, which may facilitate or maintain the binding of the polymer to surfaces of the oral cavity such as surfaces of teeth, while the bulky hydrophobic groups, such as tert-octylacrylamide and butylaminoethyl methacrylate, may provide other benefits (e.g., stain prevention) as discussed above.

As also illustrated in Table 3, the films formed from the film forming compositions (20)-(22) including DERMACRYL® 79 exhibited gloss and shine properties independent of weight percent. Although a significant difference in the gloss and shine was observed in all concentrations evaluated, the film forming composition (20), including 1 weight % of DERMACRYL® 79, provided the most consistent and reproducible results. It should be appreciated that the chemical structure of DERMACRYL® 79, similar to AMPHOMER®, includes acrylate groups that may facilitate or maintain the binding of the polymer to surfaces of the oral cavity such as surfaces of teeth, while the bulky hydrophobic groups, such as tert-octylacrylamide, may provide other benefits (e.g., stain prevention) as discussed above.

The films formed from the film forming compositions (26)-(28) including poly(ethyl acrylate-co-acrylic acid) (P(EA/AA)) exhibited gloss and shine that was dependent on the concentration (weight %) of the polymer. For example, about 10 weight % to about 20 weight % concentrations of the polymer exhibited significantly greater gloss and shine. It should be appreciated that the chemical structure of P(EA/AA) is similar to both DEMACRYL® 79 and AMPHOMER®, as P(EA/AA) possesses functional groups capable of binding to surfaces of the teeth and hydrophobic functional groups, such as the ethyl acrylate, that provide additional benefits as discussed above.

The films formed from the film forming compositions (29)-(31) including ethylcellulose AQUALON™ EC N100 surprisingly and unexpectedly exhibited variability in the gloss and shine properties. As illustrated in Table 3, the film formed from the 10 weight % film forming compositions (30) exhibited significantly less gloss and shine as compared to AMPHOMER®. Further, no significant changes in gloss and shine properties were observed for the film formed from the 1 weight % and 20 weight % film forming compositions (29) and (31), respectively. It should be appreciated that the chemical structure of ethylcellulose, unlike the other polymers, does not include any functional groups that may facilitate or maintain the binding of the polymer to surfaces of the oral cavity such as surfaces of teeth.

In view of the foregoing, it was surprisingly and unexpectedly discovered that polymers incorporating or including acrylic acid groups, which may facilitate or maintain the binding of the polymer to surfaces of the teeth, exhibited relatively greater and more reproducible or consistent gloss and shine properties.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A film forming composition for preventing stains or increasing shine and gloss of teeth, the film forming composition consisting of:
- a polymer, wherein the polymer is a copolymer of octylacrylamide and one or more monomers, wherein the one or more monomers comprises one or more of acrylic acid, methacrylic acid, and any simple ester thereof, wherein the polymer is present in an amount of about 15 weight % to about 35 weight % based on the total weight of the film forming composition; and
- an orally acceptable solvent, wherein the orally acceptable solvent comprises ethanol in a concentration of at least 74 weight % based on the total weight of the film forming composition;

wherein the composition is free of a whitening agent.

2. The film forming composition of claim 1, wherein the polymer is a copolymer of acrylates and octylacrylamide.

3. The film forming composition of claim 1, wherein the polymer is 2-propenoic acid, 2-methyl-, 2-methylpropylester, polymer with 2-propenoic acid and N-(1,1,3,3-tetramethylbutyl)-2-propenamide.

4. The composition of claim 1, wherein the polymer is present in an amount of about 18 weight %.

5. The composition of claim 1, wherein the polymer is present in an amount of about 20 weight %.

6. The composition of claim 1, wherein the orally acceptable solvent comprises ethanol in a concentration of at least 76 wt %.

* * * * *